US00PP14791P2

(12) United States Plant Patent
Williams

(10) Patent No.: US PP14,791 P2
(45) Date of Patent: May 18, 2004

(54) RHAMNUS PLANT NAMED 'RON WILLIAMS'

(50) Latin Name: *Rhamnus frangula*
Varietal Denomination: Ron Williams

(75) Inventor: Ronald Williams, Green Bay, WI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 10/624,108

(22) Filed: Jul. 21, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A new and distinct cultivar of Rhamnus plant named 'Ron Williams', characterized by its upright and columnar plant habit; freely branching growth habit; linear undulate foliage which gives a feathery appearance to the plant; low seed set; and nonviable seed.

1 Drawing Sheet

Botanical classification/cultivar designation: *Rhamnus frangula* cultivar Ron Williams.

BACKGROUND OF THE INVENTION

The present Invention relates to a new and distinct cultivar of Rhamnus plant, botanically known as *Rhamnus frangula*, and hereinafter referred to by the name 'Ron Williams'.

The new Rhamnus originated from a chance cross-pollination in 1989 of the *Rhamnus frangula* cultivar Columnaris, not patented, as the female, or seed, parent with the *Rhamnus frangula* cultivar Asplenifolia, not patented, as the male, or pollen, parent. The new Rhamnus was discovered and selected by the Inventor as a single plant in a controlled environment in Green Bay, Wisc., within a population of the progeny resulting from the cross-pollination.

Asexual reproduction of the new Rhamnus by cuttings was first conducted in Green Bay, Wisc. during the summer of 1999. Since then, asexual reproduction by cuttings has shown that the unique features of this new Rhamnus are stable and reproduced true to type in successive generations.

SUMMARY OF THE INVENTION

The cultivar Ron Williams has not been observed under all possible environmental conditions. The phenotype may vary somewhat with variations in environment such as temperature and light intensity without, however, any variance in genotype.

The following traits have been repeatedly observed and are determined to be the unique characteristics of 'Ron Williams'. These characteristics in combination distinguish 'Ron Williams' as a new and distinct Rhamnus:

1. Upright and columnar plant habit.
2. Freely branching growth habit.
3. Linear undulate foliage which gives a feathery appearance to the plant.
4. Low seed set; seed is not viable.

Plants of the new Rhamnus are most similar to plants of the female parent, the cultivar Columnaris. In side-by-side comparisons conducted in Grand Haven, Mich., plants of the new Rhamnus differed from plants of the cultivar Columnaris in the following characteristics:

1. Plants of the new Rhamnus had longer and narrower leaves than plants of the cultivar Columnaris.
2. Plants of the new Rhamnus were not as freely flowering as plants of the cultivar Columnaris.
3. Plants of the new Rhamnus produced very few seeds whereas plants of the cultivar Columnaris produced many seeds.
4. Seeds of plants of the new Rhamnus were not viable whereas seeds of plants of the cultivar Columnaris were viable.

Plants of the new Rhamnus can be compared to plants of the male parent, the cultivar Asplenifolia. In side-by-side comparisons conducted in Grand Haven, Mich., plants of the new Rhamnus differed from plants of the cultivar Asplenifolia in the following characteristics:

1. Plants of the new Rhamnus were more columnar and not as broad as plants of the cultivar Asplenifolia.
2. Plants of the new Rhamnus had longer leaves than plants of the cultivar Asplenifolia.
3. Plants of the new Rhamnus were not as freely flowering as plants of the cultivar Asplenifolia.
4. Plants of the new Rhamnus produced very few seeds whereas plants of the cultivar Asplenifolia produced a moderate amount of seeds.
5. Seeds of plants of the new Rhamnus were not viable whereas some seeds of plants of the cultivar Asplenifolia were viable.

BRIEF DESCRIPTION OF THE PHOTOGRAPH

The accompanying colored photograph illustrates the overall appearance of the new Rhamnus showing the colors as true as it is reasonably possible to obtain in colored reproductions of this type. Colors in the photograph may differ from the color values cited in the detailed botanical description which accurately describe the colors of the new Rhamnus. The photograph comprises a side perspective view of a typical plant of 'Ron Williams'.

DETAILED BOTANICAL DESCRIPTION

The aforementioned photograph and following observations and measurements describe two-year old plants grown in Grand Haven, Mich., in an outdoor nursery. During the production of the plants, day temperatures ranged from −20 to 30° C. and night temperatures ranged from −20 to 20° C. Color references are made to The Royal Horticultural Society Colour Chart, 1995 edition, except where general terms of ordinary dictionary significance are used.

Botanical classification: *Rhamnus frangula* cultivar Ron Williams.

Parentage:

*Female, or seed, parent.*—*Rhamnus frangula* cultivar Columnaris, not patented.

*Male, or pollen, parent.*—*Rhamnus frangula* cultivar Asplenifolia, not patented.

Propagation:

*Type.*—By softwood cuttings.

*Time to initiate roots.*—About 12 days at 25° C.

*Time to produce a rooted plant.*—About 90 days at 25° C.

*Root description.*—Fibrous; freely branching.

Plant description:

*Appearance.*—Perennial shrub. Upright and columnar plant habit; narrow inverted triangle. Very freely branching; with lateral branches potentially developing at every node; dense and full plants. Vigorous growth habit.

*Plant height.*—About 100 cm.

*Plant width or area of spread.*—About 40 cm.

*Lateral branches.*—Length: About 6 to 35 cm. Diameter: About 3.5 mm. Internode length: About 0.5 to 2.5 cm. Strength: Strong. Texture: Glabrous, smooth. Color: 201A.

*Foliage description.*—Arrangement: Alternate; simple. Length: About 15.5 cm. Width: About 6 cm. Shape: Linear. Apex: Acute. Base: Cuneate. Margin: Irregular, undulate. Venation pattern: Pinnate. Texture, upper and lower surfaces: Smooth, glabrous. Color: Young and fully expanded foliage, upper surface: 137A. Young and fully expanded foliage, lower surface: 137C. Venation, upper surface: 137A. Venation, lower surface: 137C. Petiole: Length: About 1.3 cm. Diameter: About 1 mm. Texture, upper and lower surfaces: Glabrous, smooth. Color, upper and lower surfaces: 161C.

Flower description:

*Appearance.*—Small single rotate flowers arranged in axillary clusters; inconspicuous; not freely flowering. Flowers not persistent. Flowers not fragrant.

*Natural flowering season.*—Plants flower during June and July in Grand Haven, Mich.

*Postproduction longevity.*—Individual flowers maintain good color and substance for about two weeks on the plant when grown in an outdoor environment.

*Flower bud.*—Length: About 3 mm. Diameter: About 3 mm. Shape: Globose. Color: 139D.

*Quantity of flowers.*—About three per cluster; about 63 flowers per plant develop during the flowering season.

*Flowers.*—Diameter: About 4 mm. Height (depth): About 4 mm.

*Petals.*—Quantity per flower: Five. Length: About 1.5 mm. Width: About 1.5 mm. Shape: Narrowly deltoid. Apex: Acute. Base: Truncate. Margin: Entire. Texture, upper and lower surfaces: Smooth, glabrous. Color: Developing petals, upper surface: 157A. Developing petals, lower surface: 177A. Fully expanded petals, upper and lower surfaces: 157A.

*Sepals.*—Sepal development has not been observed.

*Peduncles.*—Length: About 5 mm. Diameter: Less than 1 mm. Strength: Weak. Angle: About 15° from vertical. Color: 139D.

*Reproductive organs.*—Stamens: Quantity per flower: About five. Anther shape: Oblong. Anther length: About 1 mm. Pollen amount: Scarce. Pollen color: Brownish. Pistils: Quantity per flower: One, split. Pistil length: About 1 mm. Stigma shape: Spherical. Stigma color: 139D. Style length: About 1 mm. Style color: 139D. Ovary color: 139D.

*Seed.*—Plants of the new Rhamnus have not been observed to produce viable; fruits abort during development.

Disease resistance: Plants of the new Rhamnus have not been observed to be resistant pathogens common to Rhamnus.

Pest resistance: Plants of the new Rhamnus have been observed to be more resistant to Japanese Beetles compared to other cultivars of Rhamnus known to the Inventor.

Temperature tolerance: Plants of the new Rhamnus have been observed to tolerate temperatures from about −30 to 30° C.

It is claimed:

1. A new and distinct cultivar of Rhamnus plant named 'Ron Williams', as illustrated and described.

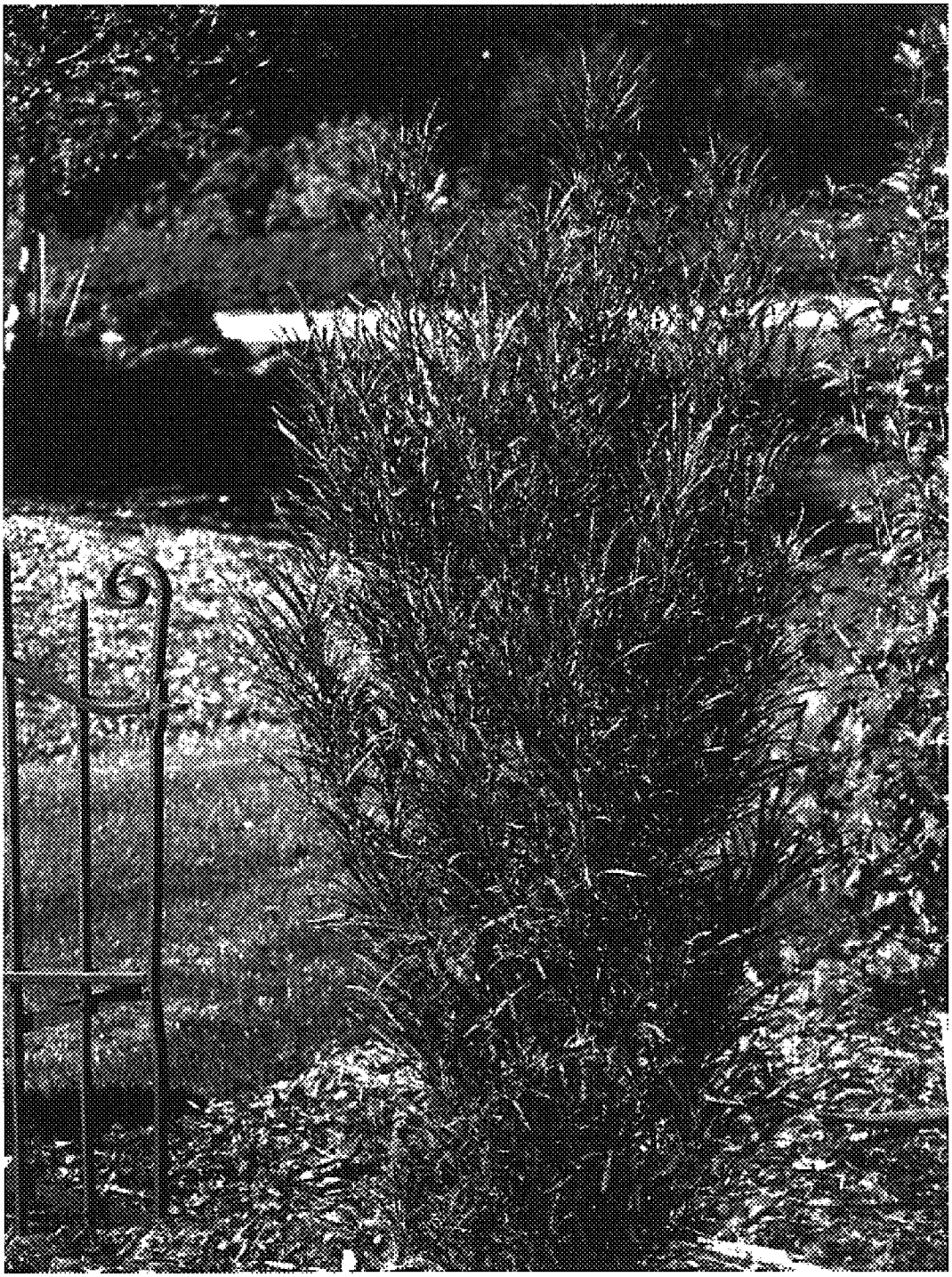

* * * * *